(12) United States Patent
Zhang et al.

(10) Patent No.: US 6,774,270 B1
(45) Date of Patent: Aug. 10, 2004

(54) METHOD OF REMOVING HEXAFLUOROPROPYLENE DIMERS

(75) Inventors: Zhongxing Zhang, Woodbury, MN (US); Zai-Ming Qiu, Woodbury, MN (US); Daniel R. Vitcak, Cottage Grove, MN (US); Richard M. Flynn, Mahtomedi, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 10/404,234

(22) Filed: Apr. 1, 2003

(51) Int. Cl.[7] .................. C07C 17/00; C07C 19/08; C07C 21/18; C07C 23/00; C07C 25/00
(52) U.S. Cl. ............... 570/151; 570/175; 570/177; 570/190; 570/191; 570/200; 570/216; 570/234; 570/236; 564/1.5; 564/248; 564/281; 564/444; 564/445; 564/463; 564/497; 564/509; 564/510
(58) Field of Search .................. 570/175, 177, 570/190, 191, 200, 216, 234, 236, 151; 564/1.5, 248, 281, 444, 445, 463, 497, 509, 510

(56) References Cited

U.S. PATENT DOCUMENTS

| | | |
|---|---|---|
| 3,185,734 A | 5/1965 | Fawcett et al. |
| 3,696,156 A | 10/1972 | Weeks |
| 5,233,107 A | 8/1993 | Jansen |
| 5,254,774 A | 10/1993 | Prokop |
| 5,300,714 A | 4/1994 | Pothapragada et al. |
| 5,462,908 A | 10/1995 | Liang et al. |
| 5,507,941 A | 4/1996 | Pothapragada et al. |
| 6,478,979 B1 | 11/2002 | Rivers et al. |
| 6,521,461 B2 | 2/2003 | Mueller et al. |

FOREIGN PATENT DOCUMENTS

| | | |
|---|---|---|
| WO | WO 99/37598 | 7/1999 |

OTHER PUBLICATIONS

England et al., Reactions of Amines with a Dimer of Hexafluoropropene and with a Perfluorovinyl Sulfide Prepared with Hexafluoropropene, Journal of Fluorine Chemistry, (1981), pp. 265–288, vol. 17.

Probst et al., Synthesis and Chemistry of Perfluoro–2–Iodo–2–Methyl–Alkanes, Journal of Fluorine Chemistry, (1987), pp. 223–245, vol. 37.

Chambers et al., "'Naked Fluoride Ion' from Elemental Fluorine", Journal of Fluorine Chemistry, (1999), pp. 213–215, vol. 94.

Brunskill et al., "Anionic Oligomerisation of Hexafluoropropene: Fission of a Carbon–Carbon Bond by Fluoride Ion", Chemical Communications, (1970), pp. 444–446.

Snegirev et al., "Reaction of Secondary Amines with Hexafluoropropylene Dimers", Bulletin of the Academy of Sciences of the USSR, Division of Chemical Science, (Nov., 1983), pp. 2305–2312, vol. 32, No. 11, Part 2.

Ishikawa et al., "Chemistry of Hexafluoroprene Oligomers", Dept. of Chemical Technology, Tokyo Institute of Technology (Ookayama, Meguro–ku, Tokyo 152), (1981), pp. 51–62, 39 (1) (translation included).

Smith et al., "The Chemistry of Carbonyl Fluoride. II. Synthesis of Perfluoroisopropyl Ketones", Journal of American Chemical Society, (Nov. 20, 1962), pp. 4285–4288, vol. 84.

*Primary Examiner*—Elvis O. Price
(74) *Attorney, Agent, or Firm*—Kent S. Kokko

(57) ABSTRACT

A method of removing hexafluoropropylene dimers ("HFP dimers"), dimer hydrides and other oligomers from a fluid is described. The method comprises heating the fluid to isomerize the HFP dimers to the thermodynamic isomer, and contacting the fluid with a tertiary amine (or salts thereof) to form a hexafluoropropylene dimer—tertiary amine adduct. The method may further comprise the step of separating the dimer adducts from the reaction mixture.

19 Claims, No Drawings

METHOD OF REMOVING HEXAFLUOROPROPYLENE DIMERS

FIELD OF THE INVENTION

This invention relates to a process for removal of hexafluoropropylene dimers and other oligomeric contaminants from fluids.

BACKGROUND OF THE INVENTION

Fluorinated fluids derived from hexafluoropropylene have many industrial uses, such as coolants for electronic devices (e.g., supercomputers), inert solvents and fluids, fire-extinguishing agents and as heat transfer agents. However, in the processes used in their preparation, or upon transient heating, many of these fluorinated fluids form oligomeric byproducts such as dimers. These dimers may be hazardous to persons handling the liquid or operating equipment containing the contaminated liquid, or may be reactive, and therefore undesirable, under conditions of use.

U.S. Pat. No. 3,696,156 describes a method of removing perfluoroolefin and perfluorochloroolefin impurities from saturated fluoroperhalocarbon compounds having two to six carbon atoms, by contacting the impure fluoroperhalocarbon in the vapor phase at about 180 to 250° C. with alumina containing a basic alkali metal or alkaline earth metal hydroxide or oxide.

U.S. Pat. No. 5,233,107 describes a process for removing olefinic impurities from hydrogen-containing chlorofluorocarbons in the gas phase at 200 to 400° C. over a zeolite. The contaminated higher boiling chlorofluorocarbons are preheated to convert the liquid to the gas phase in advance. The addition of 0.5 to 10% air or oxygen by volume to the process stream is recommended to keep coking at a very low level. One of the disadvantages of processes utilizing elevated temperatures is that they require handling hot gases contaminated with hazardous compounds. In addition, certain fluorocarbons are unstable and generate a variety of olefinic and aliphatic impurities at elevated temperatures especially in the presence of catalytic surfaces.

A system and method for purifying saturated fluoroperhalocarbon liquids by removing olefinic impurities therefrom has been disclosed in U.S. Pat. Nos. 5,300,714 and 5,507,941. Inorganic oxide, hydroxide, carbonate, or phosphate particles are used in the method.

England et al., *J Fluorine Chem.* 1981, 17, 265–288, describe reactions of amines with a dimer of hexafluoropropene and a perfluorovinyl sulfide prepared from hexafluoropropene. Anhydrous ammonia was added to a solution of hexafluoropropene dimer to form (1-amino-2,2,3,3,3-pentafluoropropylidene)propanedinitrile.

An organic amine-impregnated activated carbon composition, which preferably has been pre-treated, has been used in breathing gas filters to enhance removal of various toxic perfluorocarbons as is disclosed in U.S. Pat. No. 5,462,908. There is no disclosure as to the composition of the treated material or the nature of the nucleophile used to form a stable immobilized adduct with fluoroalkenes.

U.S. Pat. No. 6,521,461 (Mueller et al.) describes a method for removing one or more fluorinated alkenes from a fluid by contacting the fluid with an N-, S-, or P-containing nucleophile for a time sufficient to form an N-, S-, or P-containing nucleophile-fluoroalkene adduct. The nucleophile, and therefore the adduct, can be covalently bonded, coated or adsorbed to a particulate support which can be enmeshed in a porous, fibrous web.

SUMMARY OF THE INVENTION

Hexafluoropropylene (HFP) has been used in the preparation of a wide variety of useful fluorinated compounds and polymers, which are prepared by the fluoride-catalyzed addition of hexafluoropropylene to an electrophile. However, these methods invariably lead to the HFP dimeric and other oligomeric byproducts which can contaminate the desired product, may cause health or exposure risks, and are difficult to remove. Known means to remove the oligomeric byproducts are often expensive, time-consuming or involved the use of hazardous reagents. Simple distillation is often difficult due to the similar boiling points between the desired product and the undesired dimers. Distillation may also concentrate the toxic dimers and dimer hydrides. More particularly, many of the current methods are reactive with the desired reaction product as well as the undesired dimer byproduct and can reduce the yield of the desired, valuable products.

Briefly, the present invention provides a method of removing hexafluoropropylene dimers ("HFP dimers"), dimer hydrides and other oligomers from a fluid by heating the fluid to isomerize the HFP dimers to the thermodynamic isomer, and contacting the fluid with a tertiary amine (or salts thereof, preferably HF salts thereof) to form a hexafluoropropylene dimer—tertiary amine adduct. The method may further comprise the step of separating the dimer adducts from the reaction mixture.

The present invention provides a simple method of removing the undesired oligomeric byproducts using readily available materials and equipment. Advantageously, the method does not involve potentially hazardous reagents or reaction conditions, and the reagents do not substantially reduce the yields of the desired HFP-derived products.

The method is particularly useful in removing HFP dimers from fluorinated compounds derived from hexafluoropropylene, such as fluorinated ketones, HFP trimers and fluorinated aromatic compounds. Thus, the invention further provides a method of producing a fluorinated compound derived from hexafluoropropylene comprising the steps of contacting HFP with an electrophile in the presence of fluoride ion, optionally separating the crude reaction product, heating the crude reaction product to isomerize the HFP dimers, and treating the isomerized dimers with a tertiary amine (or salts thereof).

If desired, the tertiary amine may be adsorbed on, or coated on, or bonded to a support such as a porous on nonporous support. Useful supports may include a particulate support, a porous on nonporous film or web, or a foam. As used in this application:

"Adduct" or "dimer-amine adduct," means the addition product of a tertiary amine and an HFP dimer with or without the elimination of a byproduct;

"fluid" refers to a material that is a liquid at 25° C. and 760 mm Hg pressure, i.e., standard conditions;

"HFP dimer" refers to unsaturated compounds of the formula $C_6F_{12}$, formed by the dimerization of hexafluoropropylene.

"HFP dimer hydride" or "hydrides of HFP dimer" refers to compounds of the formula $C_6F_{13}H$, formed by the addition of HF to an HFP dimer.

"HFP oligomer" refers to dimers, trimers and tetramers of hexafluoropropylene;

DETAILED DESCRIPTION

Hexafluoropropylene, in the presence of fluoride ion, forms a heptafluoropropylene anion of the formula ($CF_3$—)

$_2CF^-$ that may add to a suitable electrophile to form useful fluorinated compounds. For example, the heptafluoropropylene anion may add to perfluorinated acyl fluoride to form perfluorinated ketones. However the anion may also react with hexafluoropropylene itself to form byproduct dimers, trimers and higher molecular weight oligomers that may contaminate a desired product. As noted in Probst et al., J. Fluorine Chem, 37 (1987) 223–245, the HFP dimers and dimer hydrides may represent an exposure hazard due to their toxicity.

In general, the kinetic dimer isomers of HFP form quickly in the presence of fluoride ion, and are converted to the thermodynamic dimer over time. The dimer byproducts have two kinetic isomers and a thermodynamic isomer of the following structures:

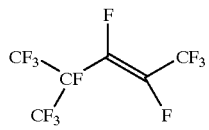

Perfluoro-E-(4-methylpent-2-ene(trans kinetic dimer)

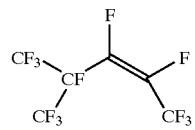

Perfluoro-Z-(4-methylpent-2-ene(cis kinetic dimer)

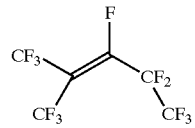

Perfluoro-2-methylpent-2-ene(thermodynamic dimer)

In the method of the invention, a fluid comprising HFP dimers is heated to isomerize the HFP dimers to the thermodynamic isomer, contacted with a tertiary amine (or salts thereof) to form a hexafluoropropylene dimer—tertiary amine adduct. In many instance the fluid may only comprise a small amount, less than 1%, of dimers or hydrides thereof. Unexpectedly, it has been found that tertiary amines do not readily add to the cis- or trans-kinetic dimers at an appreciable rate, but do add to the thermodynamic dimer. Thus, the dimer isomers may be removed by first isomerizing the mixture followed by treatment with the tertiary amine (or salt thereof). HFP dimer hydrides are also removed by the method of the invention. It is believed that the hydrides are dehydrofluorinated under the reaction conditions to produce the HFP dimers.

The isomerization may be catalyzed by fluoride ion, which may be added to the fluid. In many instance however, additional fluoride may not be necessary, the fluid may contain sufficient fluoride ion to effect the isomerization as result of the means of preparation. For example, in the preparation of a perfluorinated ketone, fluoride ion is eliminated from the perfluorinated acyl fluoride on addition of the heptafluoropropylene anion. Many commercial fluorinated fluids have minor amount of fluoride ion present due to their means of manufacture. Normally fluoride amounts of 0.5 to 10 wt. % relative to the total weight of the dimers present are sufficient to isomerize the kinetic dimers to the thermodynamic dimer, although greater amounts may be used.

Useful sources of fluoride ion include simple and complex inorganic fluoride salts, simple and complex organic fluoride salts or combinations thereof. Particularly useful inorganic fluoride salts are alkali- and alkali-earth fluoride salts such as sodium, potassium, cesium fluoride and calcium fluoride. Organic fluoride salts may include ammonium fluoride, as well as mono-, di-, tri and tetralkyl ammonium fluorides.

Other nucleophiles may also be used to effect the isomerization, for examples halides such as bromides, chlorides, and amines. However it is believed that such nucleophiles undergo an addition/elimination reaction with the dimer to release a fluoride ion, which further catalyzes the isomerization. Thus, any nucleophile that may undergo an addition elimination reaction with the dimers with concomitant elimination of fluoride ion may be used to effect the catalytic isomerization. Further, the fluoride-catalyzed isomerization may be enhanced by the addition of a phase transfer catalyst. In some fluids the solubility of the fluoride is low, and the addition of a phase transfer agents may beneficially increase the solubility and enhance the rate of isomerization. Useful phase transfer agents include, for example, tetralkyl ammonium halides such as ADOGEN™ 464, available from Aldrich Chemical.

The isomerization may be conducted at a temperature of from 75 to 150° C. Lower temperatures including room temperature may be used, but the rates may be too slow for an acceptable commercial process. Preferably, the temperature is at least 100° C.

The time required is dependent on the fluoride ion concentration, the concentration of dimers present, the volume of fluid to be treated and the temperature, which are generally selected so the isomerization occurs in less than a day, preferably in 1 to 6 hours time.

The tertiary amine for forming the HFP-amine adducts may be mono-, di-, or polyamine. The amines may be polymeric compounds having terminal or pendent tertiary amino groups. The simplest tertiary amine is trimethylamine and this compound, and its $C_2$, $C_3$, $C_4$ to $C_\Omega$ homologues can be used. It is of course possible to use tertiary amines containing a mixture of alkyl groups, for instance methyldiethanolamine. The tertiary amine can contain more than one tertiary amine moiety. It may also contain other functional groups provided that those other functional groups do not interfere with the required reaction, or the functional groups participate beneficially in the required reaction. An example of a functional group that does not interfere is an ether group.

Useful tertiary amines include, for example, N-methyl morpholine, bis-(2-dimethylaminoethyl)ether, 1-methyl-4-dimethylaminoethyl piperazine, dimethyl benzylamine, triethylamine, methyldiethylamine, trimethylamine, phenylmethylethylamine, dimethylpropylamine, pyridine, 10-dimethylaminopyridine, imidazoles such as 2-ethylimidazole and 2-ethyl-4-methylimidazole, guanidines such as tetramethyl guanidine; 1,3,5-tris (dimethylaminopropyl)hexahydro-s-triazine, pentamethyldipropylenetriamine, pentamethyldiethylenetriamine, dimethylcyclohexylamine, 1,8-diazabicyclo(5,4,0)-undec-7-ene (DBU), 1,4-diazabicyclo(2,2,2)octane, tetraethyltriethylene diamine, methylene-bis(cyclohexyl amine), N,N,N,N-tetrabutyl ethylenediamine, tetramethylenethylene diamine, dipiperdinomethane, tetramethyldiaminomethane and pentamethyldiethylene triamine and the like. Suitable polymeric amines include those tertiary amine derived from polyvinylamine, polyethylenediamine, polypropylenediamine and polyallylamine The tertiary amine may be in the form of an amine salt, i.e. a quaternary amine salt, which may have an organic or inorganic anion. The salts of the invention are ammonium, and organic or inorganic tertiary amine salts and can be prepared by treating the tertiary amine with an appropriate acid under mild conditions. Although the quaternary amine may comprise other organic or inorganic anions, fluoride is preferred. Most preferred are hydrogen fluoride salts of tertiary amines.

The tertiary amine is generally added in molar amounts equivalent to, or in excess of, the amount of dimers present. As contaminate dimer is usually 5 wt. % or less of the reaction product, these amounts of tertiary amines do no substantially reduce the yield of the desired fluorinated products, even if they are reactive toward the desired products. Usually 1 to 5 times amine relative to the amount of dimer present in the fluid is sufficient (on a molar basis). The amount used does not usually exceed 5 wt. % of the weight of the fluid to be treated. Using the process of this invention, a fluid may be treated to reduce the amount of dimers present to less than 5000 ppm, preferably less than 1000 ppm, and most preferably less than 500 ppm. Certain fluid specification may require lower limits, such as 100 ppm, which can be achieved using the method of this invention. The amount of dimer in a fluid may be determined by conventional analytic means, such as gas chromatography/mass spectroscopy, IR, $^1$H and $^{19}$F NMR. Useful temperatures for HFP-amine adduct formation are from room temperature and above, e.g. 20 to 100° C.

The dimer-amine adduct may comprise a mixture of compounds. Without wishing to be bound by theory, it is believed that the amine adds to the double bond of the dimer to form a zwitterionic intermediate, which may eliminate to form a vinyl ammonium compound, or may be protonated to form a β-hydroamino compound. Alternatively, the dimer hydride compound may react with the tertiary amine to form a salt, or may react by dehydrofluorination to produce one or more unsaturated dimer isomers. Where amine salts are used, they are believed to hydrofluorinated the double bond to form the dimer hydrides.

If desired, the tertiary amine (or salt thereof) may be adsorbed on, coated onto or bonded directed to a porous or nonporous matrix. The matrix may in the form of a column or cartridge through which the fluid may pass to be treated. The use of such a matrix may facilitate separation of the dimer-amine adduct from the treated fluid or the desired fluorinated product.

Although the steps of isomerization and adduct formation are preferentially sequential, the steps may occur simultaneously whereby a fluid is treated with fluoride ion and a tertiary amine, or hydrogen fluoride salt of a tertiary amine, at room or elevated temperatures.

The present invention is particularly useful in removing undesired dimers, and dimer hydrides, from a reaction product derived from hexafluoropropylene. As known, hexafluoropropylene will form the weakly nucleophilic heptafluoropropylene anion, which may add to a strongly electrophilic compound to form useful fluorinated products. Useful electrophiles include other fluorinated olefins such as tetrafluoroethylene, perfluorobutene, perfluorinated-, nonfluorinated- or partially fluorinated acyl compounds, including, acyl halides, esters, and anhydrides; and fluorinated aromatic compounds.

Fluorinated ketones (i.e., perfluoroketones) may be prepared as described in, for example, U.S. Pat. No. 3,185,734 (Fawcett et al.) and J. Am. Chem. Soc., v. 84, pp. 4285–88, 1962, by hexafluoropropylene addition to a perfluoroacyl halide (e.g., $CF_3CF_2COF$) in an anhydrous environment (e.g., in diethylene glycol dimethyl ether, or "diglyme") in the presence of anhydrous fluoride ion at an elevated temperature, typically at around 50 to 80° C. The diglyme/fluoride ion mixture can be recycled for subsequent fluorinated ketone preparations, e. g., to minimize exposure to moisture. When this reaction scheme is employed, hexafluoropropylene dimer and/or trimer is produced as a by-product in the branched perfluoroketone product. The amount of dimer and/or trimer may be reduced by gradual addition of hexafluoropropylene to the perfluoroacyl halide over an extended time period, e.g., several hours.

Such perfluorinated ketones are useful as fire extinguishing compositions for the replacement of bromine-containing compounds such as HALON 1301 and HALON 1211 as described in U.S. Pat. No. 6,478,979 (Rivers et al). In the preparation of $(CF_3)_2CF$—CO—$CF_2CF_3$, the product is contaminated by byproduct dimers, which must be reduced to meet safety standards. Distillation is ineffective due to the close boiling points of the trans- and cis-kinetic isomers (~46° C.), the thermodynamic isomer (~50° C.) with the desired product (~49° C.), but may be removed by the method of this invention.

Fluorinated acyl fluorides are well known and can be prepared by electrochemical fluorination (ECF) of a corresponding hydrocarbon carboxylic acid (or a derivative thereof, using either anhydrous hydrogen fluoride (Simons ECF) or KF/2HF (Phillips ECF) as the electrolyte. Fluoroalkyl esters and fluoroalkyl carbonates are also well known in the chemical art, and can be prepared from fluorinated acyl fluorides, or can be directly prepared by known methods such as fluorination of an appropriate organic precursor.

Examples of compounds that can be useful as fluorinated electrophiles include fluorinated acyl fluorides, fluorinated acyl chlorides, fluoroalkyl esters, fluorinated anhydrides, and fluoroalkyl carbonates, and are exemplified as follows: $CF_3C(O)F$, $C_2F_5C(O)F$, $C_3F_7C(O)F$, $C_4F_9C(O)F$, $C_5F_{11}C(O)F$, $CF_3C(O)Cl$, $C_2F_5C(O)Cl$, $C_3F_7C(O)Cl$, $C_4F_9C(O)Cl$, $C_5F_{11}C(O)Cl$, $CF_3CO_2CF_3$, $C_2F_5CO_2C_2F_5$, $C_4F_9CO_2C_4F_9$, $C_5F_{11}CO_2C_5F_{11}$, $CF_3C(O)$—O—$C(O)CF_3$, $C_2F_5C(O)$—O—$C(O)C_2F_5$, $C_3F_7C(O)$—O—$C(O)C_3F_7$, $C_4F_9C(O)$—O—$C(O)C_4F_9$, $C_5F_{11}C(O)$—O—$C(O)C_5F_{11}$, $CF_3OC(O)OCF_3$, $CF_3CF_2OC(O)OCF_2CF_3$, $C_3F_7OC(O)OC_3F_7$, as well as partially fluorinated analogues thereof.

Fluorinated compounds may be prepared by contacting HFP with an electrophile in the presence of fluoride ion. Generally, heating of the reaction fluid is preferred, although the reaction can proceed at ambient temperature. Still, any temperature between 0 to 100° C. may be used. Mild heating e.g., to about 60° C. or higher, can be useful to cause production of the heptafluoropropylene anion, or to increase reaction rate of the anion and the electrophile. The course of the reaction can be monitored using standard analytical techniques, e.g., gas chromatography, to observe conversion of the reactants and product formation.

Thus, the present invention provides a method of producing a fluorinated product derived from hexafluoropropylene by contacting hexafluoropropylene with fluoride ion in the presence of an electrophile to produce the desired fluorinated product and undesired dimers (or dimer hydrides, and other oligomers such as trimers), heating the reaction mixture in the presence of fluoride ion (or other suitable isomerization catalyst) to isomerize the dimers, then contacting the reaction mixture with a tertiary amine (or salt therof) to produce the dimer-amine adduct.

If desired, the fluid to be treated may further comprise a polar aprotic solvent. Solvents are chosen to be non reactive with either the dimer, the dimer adduct or the desired reaction product. Suitable polar aprotic solvents include acyclic ethers such as diethyl ether, ethylene glycol dimethyl ether, and diethylene glycol dimethyl ether; carboxylic acid esters such as methyl formate, ethyl formate, methyl acetate, diethyl carbonate, propylene carbonate, and ethylene carbonate; alkyl nitriles such as acetonitrile; alkyl amides such as N,N-dimethylformamide, N,N-diethylformamide, and N-methylpyrrolidone; alkyl sulfoxides such as dimethyl sulfoxide; alkyl sulfones such as dimethylsulfone, tetramethylene sulfone, and other sulfolanes; oxazolidones such as N-methyl-2-oxazolidone; and mixtures thereof.

The dimer-amine adduct may be separated from solution using conventional means know to the art. In one embodiment, the fluid to be treated comprises a solvent in which the fluorinated product or the dimer-amine adduct is soluble, but not both. In this embodiment, for example, a solvent is chosen so that the dimer adduct is soluble in the chosen solvent, but the desired product is not. Alternatively, the solvent may be chosen so that the desired product is soluble in the chosen solvent, but the dimer adduct is not. In another embodiment, the fluid to be treated is contacted with silica or alumina having a preferential affinity for the adduct. In another embodiment the product fluorinated compound is distilled from the fluid, optionally as an azeotrope. Where a hydrogen fluoride tertiary amine salt is used to generate the amine-dimer adduct, distillation temperatures are preferably kept below the decomposition temperature of the adduct. In another embodiment, the dimer-amine adduct may precipitate or "phase-split" from the treated fluid and may be separated by decantation.

EXAMPLES

For purposes of the following examples, all percentages are given as an area % of a gas chromatrography—flame ionization detector analysis (GC-FID). This area % very closely approximates the weight percent.

Preparation of 1,1,1,2,2,4,5,5,5-nonofluoro-4 trifluoromethyl pentane-3-one $CF_3CF_2C(O)CF(CF_3)_2$ A crude $C_6$ perfluorinated ketone $(CF_3CF_2C(O)CF(CF_3)_2)$ can be made according to methods described in U.S. Pat. No. 6,478,979. $C_2F_5COF$ was reacted with HFP using diglyme as the solvent and KF as the catalyst. The crude $C_6$ perfluoroketone contained HFP trans-kinetic dimer, HFP cis-kinetic dimer, HFP thermodynamic dimer, and dimer hydride $((CF_3)_2CH-CF_2CF_2CF_3)$ as impurities. The term "$C_6$ PFK" used in the following examples refers to the crude $C_6$ perfluorinated ketone prepared with this method.

Example 1
Conversion of Kinetic Dimers to Trimers and Thermodynamic Dimer 300 g of crude $C_6$ perfluoroketone were added to a 600 ml stainless steel Parr reactor equipped with stirrer, heater and thermocouple. The crude $C_6$ perfluoroketone had the following impurities as analyzed by gas chromatography (GC-FID): HFP trans-kinetic dimer—0.57%, HFP cis-kinetic dimer—0.06%, HFP thermodynamic dimer—0.24%, dimer hydride—0.02%, and HFP trimers—0.31%. 30 g of KF (Aldrich) and 150 g of diglyme (Aldrich) were also added to the Parr reactor. The mixture in the reactor was heated to 140° C. with stirring and held at this temperature for 6 hours. The reaction mixture was then cooled to room temperature. GC analysis of the $C_6$ perfluoroketone phase showed the following: HFP trans-kinetic dimer—0.12%, HFP cis-kinetic dimer—0.06%, HFP thermodynamic dimer—0.43%, dimer hydride—0.02%, and HFP trimers—0.35%.

Example 2
Conversion of Kinetic Dimers to Trimers and Thermodynamic Dimer using quaternary ammonium salt 300 g of the crude $C_6$ PFK (see Example 1), 30 g of KF, 150 g of diglyme, and 6 g of Adogen/diglyme (50/50 by weight) were charged to a Parr reactor equipped with stirrer, heater and thermocouple. The Adogen/diglyme was prepared by stripping residual alcohol away from Adogen 464 (a methyltrialkyl quaternary ammonium chloride phase transfer catalyst available from Aldrich) in the presence of diglyme. The mixture in the reactor was heated to 105° C. with stirring and held at this temperature for 6 hours. The reaction mixture was then cooled to room temperature. GC analysis of the $C_6$ perfluorinated ketone phase showed the following: HFP trans-kinetic dimer—0.03%, HFP cis-kinetic dimer—0.04%, HFP thermodynamic dimer—0.36%, dimer hydride—0.02%, and HFP trimers—0.48%.

Example 3
Conversion of Kinetic Dimers to Trimers using quaternary ammonium salt 300 g of crude $C_6$ PFK were charged to a 600 ml stainless steel Parr reactor equipped with stirrer, heater and thermocouple. The crude $C_6$ PFK had the following impurities as analyzed by GC; HFP trans-kinetic dimer—0.81%, HFP cis-kinetic dimer—0.16%, HFP thermodynamic dimer—0.81%, dimer hydride—0.04%, and HFP trimers—0.83%. 30 g of KF, 150 g of diglyme, and 6 g of Adogen/diglyme (50/50 by weight as prepared in example 2) were also charged to the reactor. The mixture in the reactor was heated to 130° C. with stirring and held at that temperature for 6 hours. The reaction mixture was then cooled to room temperature. GC analysis of the resulting $C_6$ perfluorinated ketone phase showed the following: HFP trans-kinetic dimer—0.06%, HFP cis-kinetic dimer—0.14%, HFP thermodynamic dimer—0.64%, dimer hydride—0.04%, and HFP trimers—1.23%.

Example 4
Conversion of Kinetic Dimers to Trimers and Thermodynamic Dimer using tributylamine 300 g of the crude $C_6$ PFK (see Example 3), 30 g of KF, 150 g of diglyme, and 2 g of tributylamine (Aldrich) were charged to a Parr reactor equipped with stirrer, heater and thermocouple. The mixture in the reactor was heated to 105° C. with stirring and held at that temperature for 6 hours. The reaction mixture was then cooled to room temperature. GC analysis of the resulting $C_6$ perfluorinated ketone phase showed the following: HFP trans-kinetic dimer—0.17%, HFP cis-kinetic dimer—0.06%, HFP thermodynamic dimer—0.98%, dimer hydride—0.09%, and HFP trimers—1.03%.

Example 5
Preparation of HFP thermodynamic dimer $(CF_3)_2C=CFCF_2CF_3$

To a 2 liter flask fitted with a stirrer, thermowatch and condenser was added 5.8 grams of cesium fluoride (Aldrich), 100 grams of methyl sulfoxide (Aldrich) and 10 grams of Adogen/diglyme (50/50 by weight as described in Example 2). 1926 g of kinetic HFP dimers (prepared according to U.S. Pat. No. 5,254,774) were added to the solution that was then heated to reflux, 48° C. and held overnight with agitation. The material was purified by fractional distillation from the reactor to yield 1548 grams of material boiling between 50–51° C. and contained 97.8% thermodynamic dimer. 510 grams of this material was retreated with 100 grams of diglyme, 100 grams of potassium fluoride and 62.4 grams of a phase transfer catalyst (PTC) solution in a Parr reactor set at 75° C. and held for 17 hours. The product was distilled from the Parr reactor, washed 3 times with water and fractionated to yield 80 grams of 99.4% thermodynamic dimer as determined by NMR analysis. The PTC solution was the reaction product of equal molar amounts of tripentyl amine (97% mixture of isomers from Sigma-Aldrich Corp., St. Louis Mo.), and dimethylsulfate (Aldrich) reacted at 60° C. overnight in a 50% solution with diglyme.

Example 6
Removal of HFP thermodynamic dimer by Tetramethyldiaminomethane (TMDM)

A masterbatch of 0.43% thermodynamic dimer was prepared by dosing the thermodynamic dimer prepared in Example 5 into pure Novec 1230™ fire extinguishing fluid (3M Company, St. Paul, Minn.). A 40-gram aliquot of this masterbatch was treated with TMDM (2.2 grams, 0.215 moles from Sigma Aldrich, St Louis Mo.) in a 100 ml flask and heated to 49° C. with magnetic stirring for 2 hours. The reaction mixture was then cooled to room temperature, transferred to a separatory funnel to yield 97.6% of the starting masterbatch. GC-FID analysis of the resulting $C_6$ perfluorinated ketone showed that thermodynamic HFP dimer had been reduced to less than the FID detection limit of 10 ppm. No dimer hydride was observed.

Example 7
Removal of HFP thermodynamic dimer by Tetramethylethylenediamine (TMEDA)

A 40 g aliquot of the same masterbatch prepared in Example 6 was treated with 2.3 g TMEDA (Sigma Aldrich, St. Louis Mo.) as described in Example 6. 80% of the resulting starting material was recovered from the phase split and a GC-FID analysis showed that thermodynamic dimer was reduced to less than the FID detection limit of 10 ppm. No dimer hydride was observed.

Example 8
Removal of HFP thermodynamic dimer and Dimer hydride by 1.8-Diazabicyclo[5.4.0]undec-7-ene (DBU)

250 g of crude $C_6$ perfluoroketone were placed in a 250 ml plastic bottle. The crude $C_6$ perfluoroketone contained 0.4% thermodynamic HFP dimer and 0.07% dimer hydride. 7 g of DBU (Aldrich) was added to the bottle. The bottle was sealed, placed on a shaker and shaken for 2 hours at room temperature. GC analysis of the resulting $C_6$ perfluoroketone showed that thermodynamic HFP dimer and dimer hydride had both been reduced to less than 10 ppm.

Example 9
Removal of HFP thermodynamic dimer and Dimer hydride by Pentamethyldiethylenetriamine 250 g of crude $C_6$ perfluoroketone (same as used in example 8) were placed in a 250 ml plastic bottle. 7 g of pentamethyldiethylenetriamine (Aldrich) and 25 g of diglyme were added to the bottle. The bottle was sealed, placed on a shaker and shaken for 2 hours at room temperature. GC analysis of the resulting $C_6$ perfluoroketone showed that thermodynamic HFP dimer and dimer hydride had both been reduced to less than 10 ppm.

Example 10
Removal of HFP thermodynamic dimers and HFP trimers by 1.8-Diazabicyclo[5.4.0]undec-7-enc (DBU)

250 g of crude $C_6$ perfluoroketone were placed in a 600 ml stainless steel Parr reactor equipped with stirrer, heater and thermocouple. The $C_6$ perfluoroketone contained 0.4 wt % thermodynamic HFP dimer and 1.0 wt % HFP trimers as analyzed by GC. 3 g of DBU and 25 g of diglyme were added to the Parr reactor. The mixture in the reactor was heated to 93° C. with agitation and held at this temperature for 16 hours with continued stirring. The reaction mixture was then cooled to room temperature. GC analysis of the resulting $C_6$ perfluoroketone showed that thermodynamic HFP dimer had been reduced to less than 10 ppm and HFP trimers had been reduced to less than 0.1 wt %.

Example 11
Use of primary amine to remove HFP thermodynamic dimer from hydrofluoroether (HFE)

30 g of HFE 7100 hydrofluoroether (3M Company) was placed in a 30 ml poly bottle. The HFE 7100 was dosed with HFP kinetic dimers (prepared as in U.S. Pat. No. 5,254,774) and HFP thermodynamic dimers (prepared in example 5) so that it contained 8,000 ppm HFP kinetic dimer, 3,200 ppm HFP thermodynamic dimer, and 15 ppm dimer hydride of thermodynamic HFP dimer. 1.2 g of allylamine (Aldrich) were added to the bottle. The bottle was sealed, placed on a shaker and shaken for 2 hours at room temperature. GC analysis of the resulting HFE 7100 showed that the HFP thermodynamic dimer was reduced to 17 ppm, Dimer hydride was non-detectable and the HFP kinetic dimers were unchanged.

Example 12
Use of secondary amine to remove HFP thermodynamic dimer from hydrofluoroether (HFE)

30 g of HFE 7100 hydrofluoroether dosed with HFP dimers (as described in Example 11) was placed in a 30 ml poly bottle. 1.2 g of morpholine (Aldrich) were added to the bottle. The bottle was sealed, placed on a shaker and shaken for 2 hours at room temperature. GC analysis of the resulting HFE 7100 showed that the HFP thermodynamic dimer was reduced to 26 ppm and the HFP kinetic dimers were unchanged.

Example 13
Use of tertiary amine to remove HFP thermodynamic dimer from hydrofluoroether (HFE)

30 g of HFE 7100 dosed with HFP dimers (as described in Example 11) was placed in a 30 ml poly bottle. 1.2 g of 1,8-diazabicyclo[5.4.0]undec-7-ene (DBU) were added to the bottle. The bottle was sealed, placed on a shaker and shaken for 2 hours at room temperature. GC analysis of the resulting HFE 7100 showed that the HFP thermodynamic dimer was reduced to 300 ppm and the HFP kinetic dimers were unchanged.

What is claimed is:

1. A method of removing hexafluoropropylene dimers from a solution comprising the steps of:
   a. isomerizing said dimers to the thermodynamic isomer,
   b. contacting the solution with a tertiary amine or tertiary amine salt to form the amine-dimer adducts, and
   c. removing said adducts from solution.

2. The method of claim 1 wherein said step of isomerizing comprises contacting said dimers with a catalytic amount of fluoride ion for a time and a temperature sufficient to effect said isomerization.

3. The method of claim 2 wherein said fluoride is generated in situ by an addition/elimination reaction of a nucleophile with the dimers.

4. The method of claim 2 wherein the fluoride ion comprises 0.5 to 10 wt. %, relative to the total weight of the dimers present.

5. The method of claim 2 wherein said step of isomerizing comprises maintaining said solution at an elevated temperature.

6. The method of claim 2 wherein said step of isomerizing comprises heating said solution at a temperature of at least 100° C.

7. The method of claim 1 wherein said tertiary amine is selected from N-methyl morpholine, bis-(2-dimethylaminoethyl)ether, 1-methyl-dimethylaminoethyl piperazine, dimethyl benzylamine, triethylamine, methyldiethylamine, trimethylamine, phenylmethylethylamine, dimethylpropylamine, pyridine, 10-dimethylaminopyridine, imidazoles such as 2-ethylimidazole and 2-ethyl-4-methylimidazole, tetramethyl guanidine; 1,3,5-tris(dimethylaminopropyl) hexahydro-s-triazine, pentamethyldipropylenetriamine, pentamethyldiethylenetriamine, dimethylcyclohexylamine, 1,8-diazabicyclo(5,4,0)-undec-7-ene (DBU), 1,4-diazabicyclo(2,2,2)octane, tetraethyltriethylene diamine, methylene-bis(cyclohexyl amine), N,N,N,N-tetrabutyl ethylenediamine, tetramethyl-tetramethylenethylene diamine, dipiperidinomethane, tetramethyldiaminomethane and pentamethyldiethylene triamine, mixtures and salts thereof.

8. The method of claim 1 wherein said amine-dimer adduct is removed by decantation.

9. The method of claim 1 wherein said amine-dimer adduct is removed by distillation.

10. The method of claim 1 wherein said solution comprises the reaction product of hexafluoropropylene with a perfluorinated acyl compound.

11. The method of claim 1 further comprising the step of adding a solvent to reduce the solubility of the amine-dimer adduct in said solution.

12. The method of claim 2 wherein said isomerization is conducted in the presence of a phase transfer catalyst.

13. The method of claim 12 where said phase transfer catalyst is a tetralkyl ammonium halides.

14. The method of claim 1 wherein said thermodynamic dimer is selectively removed from a mixture of thermodynamic and kinetic dimers.

15. The method of claim 2 wherein said isomerization is conducted in the presence of a solvent.

16. A method of preparing a fluorinated compound comprising the steps of a. contacting hexafluoropropylene with an electrophile compound in the presence of fluoride ion, b. heating the reaction mixture to isomerize hexafluoropropylene dimers produced to the thermodynamic isomer, c. contacting the solution with a tertiary amine or tertiary amine salt to form the amine-dimer adducts, and d. separating said adducts from the fluorinated compound.

17. The method of claim 16 wherein the fluorinated compound is a perfluorinated ketone.

18. The method of claim 17 wherein said electrophile is a perfluorinated acyl halide, a perfluorinated ester, or a perfluorinated anhydride.

19. The method of claim 1 wherein the solution after step c has less than 1000 ppm dimers.

* * * * *

UNITED STATES PATENT AND TRADEMARK OFFICE
CERTIFICATE OF CORRECTION

| | | |
|---|---|---|
| PATENT NO. | : 6,774,270 B1 | Page 1 of 1 |
| APPLICATION NO. | : 10/404234 | |
| DATED | : August 10, 2004 | |
| INVENTOR(S) | : Zhongxing Zhang | |

It is certified that error appears in the above-identified patent and that said Letters Patent is hereby corrected as shown below:

Title Page, Column 2
Item [56] Under "(Other Publicaitons)" line 6, delete "Iodo" and insert -- Iodo --, therefor.

Column 4
Lines 37-38, delete "methyldiethanolamine" and insert -- methyldiethylamine --, therefor.

Column 9
Line 37, delete "1.8" and insert -- 1,8 --, therefor.
Line 61, delete "1.8" and insert -- 1,8 --, therefor.
Line 61, delete "-enc" and insert -- -ene --, therefor.

Column 11
Line 6, in Claim 7, delete "1-methyl-dimethylaminoethyl" and insert
-- -1-methyl-4-dimethylaminoethyl --, therefor.

Signed and Sealed this

Seventeenth Day of April, 2007

JON W. DUDAS
*Director of the United States Patent and Trademark Office*